(12) United States Patent
Doyle et al.

(10) Patent No.: US 9,618,447 B2
(45) Date of Patent: Apr. 11, 2017

(54) OPTICAL TRANSMISSION CELL WITH MINIMIZED SPURIOUS ABSORPTION

(71) Applicant: HELLMA HOLDING GMBH, Muellheim (DE)

(72) Inventors: Walter M. Doyle, Tustin, CA (US); Norman A. Jennings, Tustin, CA (US)

(73) Assignee: HELLMA HOLDING GMBH, Muellheim (DE)

( * ) Notice: Subject to any disclaimer, the term of this patent is extended or adjusted under 35 U.S.C. 154(b) by 0 days.

(21) Appl. No.: 14/660,762

(22) Filed: Mar. 17, 2015

(65) Prior Publication Data

US 2015/0260638 A1 Sep. 17, 2015

Related U.S. Application Data

(60) Provisional application No. 61/954,464, filed on Mar. 17, 2014.

(51) Int. Cl.

| G01N 21/3504 | (2014.01) |
|---|---|
| G01N 33/00 | (2006.01) |
| G01N 21/05 | (2006.01) |
| G01N 21/359 | (2014.01) |
| G01N 21/03 | (2006.01) |

(52) U.S. Cl.
CPC ......... *G01N 21/3504* (2013.01); *G01N 21/05* (2013.01); *G01N 21/359* (2013.01); *G01N 33/0059* (2013.01); *G01N 21/0317* (2013.01); *G01N 2021/0389* (2013.01); *G01N 2201/0227* (2013.01)

(58) Field of Classification Search
CPC .. G01N 21/3504; G01N 21/359; G01N 21/05; G01N 33/0059; G01N 21/0317; G01N 2201/0227; G01N 2021/0389
USPC ....................................................... 250/338.1
See application file for complete search history.

(56) References Cited

U.S. PATENT DOCUMENTS

| 4,507,954 A * | 4/1985 | Boutwell ............... G01M 3/223 73/40.7 |
|---|---|---|
| 5,442,437 A * | 8/1995 | Davidson ............... G01N 21/05 356/246 |

* cited by examiner

*Primary Examiner* — David Porta
*Assistant Examiner* — Gisselle Gutierrez
(74) *Attorney, Agent, or Firm* — Myers Andras LLP; Joseph C. Andras

(57) ABSTRACT

A spectroscopic measuring device for minimizing spurious absorption due to undesired gases. The device includes a probe body, or a transmission cell formed from a central measurement cell and first and second probe bodies. Each probe body is subject to leakage of undesired gas, especially over time in the presence of high pressure gas. Each probe body includes a bore located between a primary window disposed at or near a distal end and a secondary window located at or near the proximal end. It being observed that the absorbance is proportional to the pathlength and inversely proportional to the volume as long as the pressure in the probe body remains low compared to that in the measurement cell, a glass filler rod is located in the bore and a is void located adjacent to the filler glass rod, thereby minimizing spurious absorption even in the presence of leakage.

8 Claims, 2 Drawing Sheets

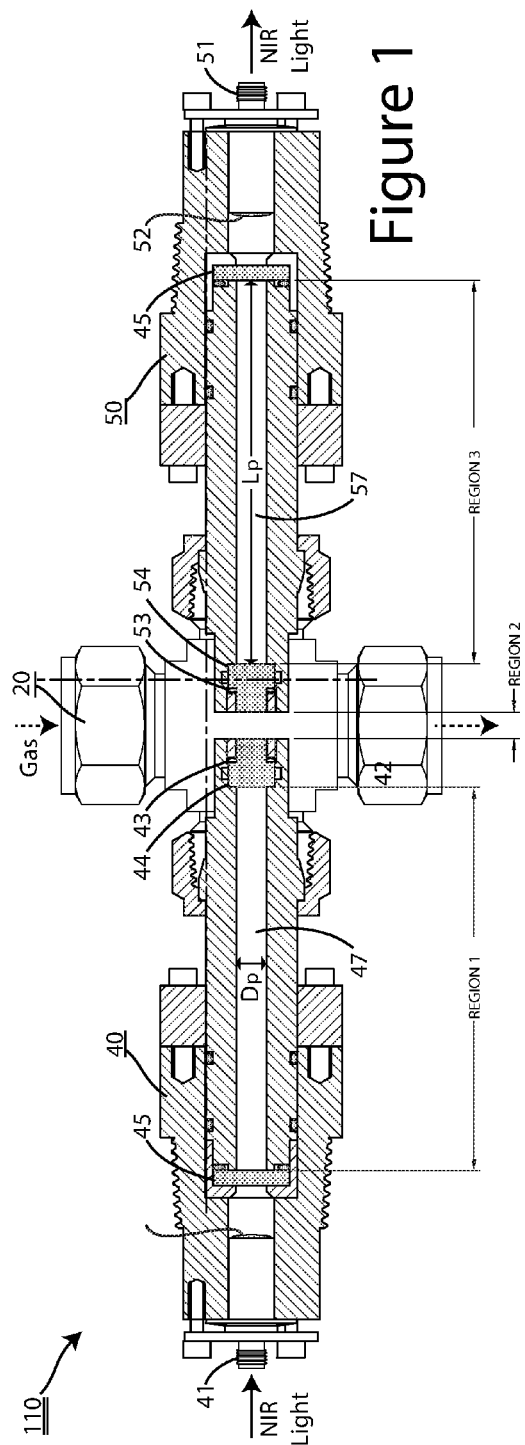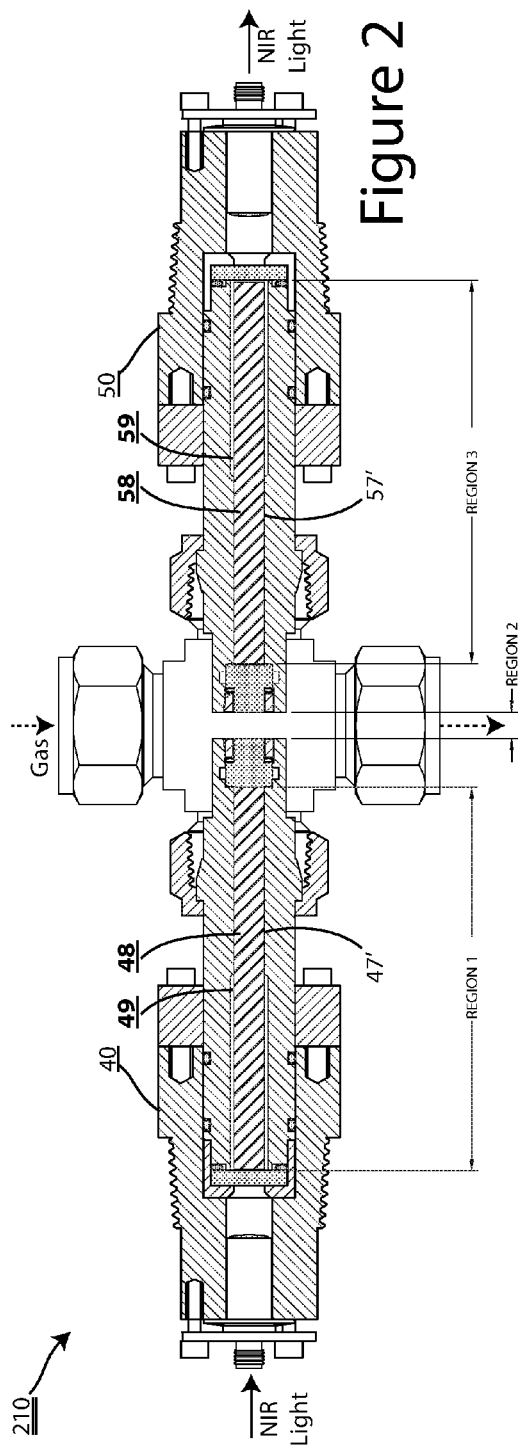

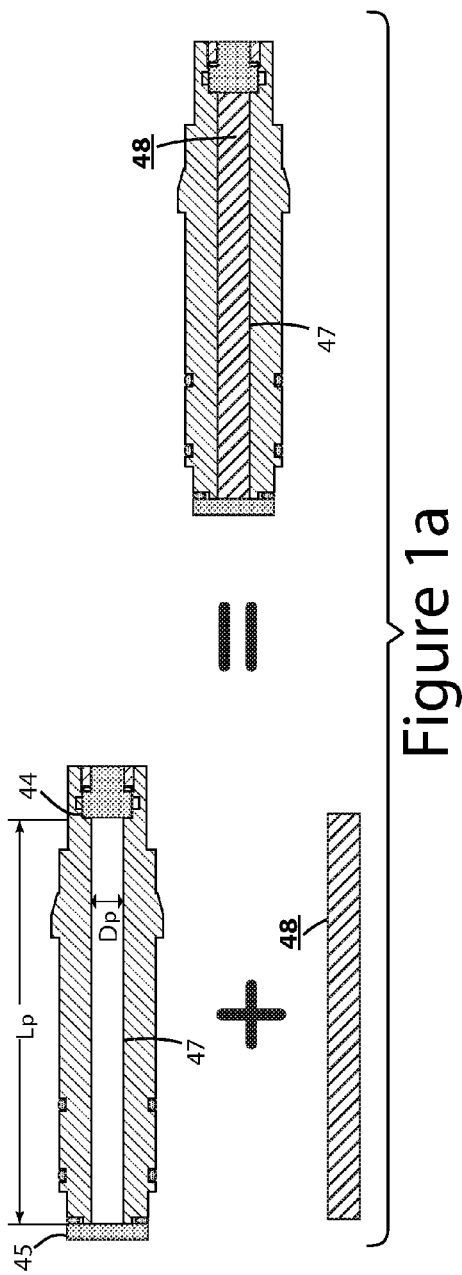
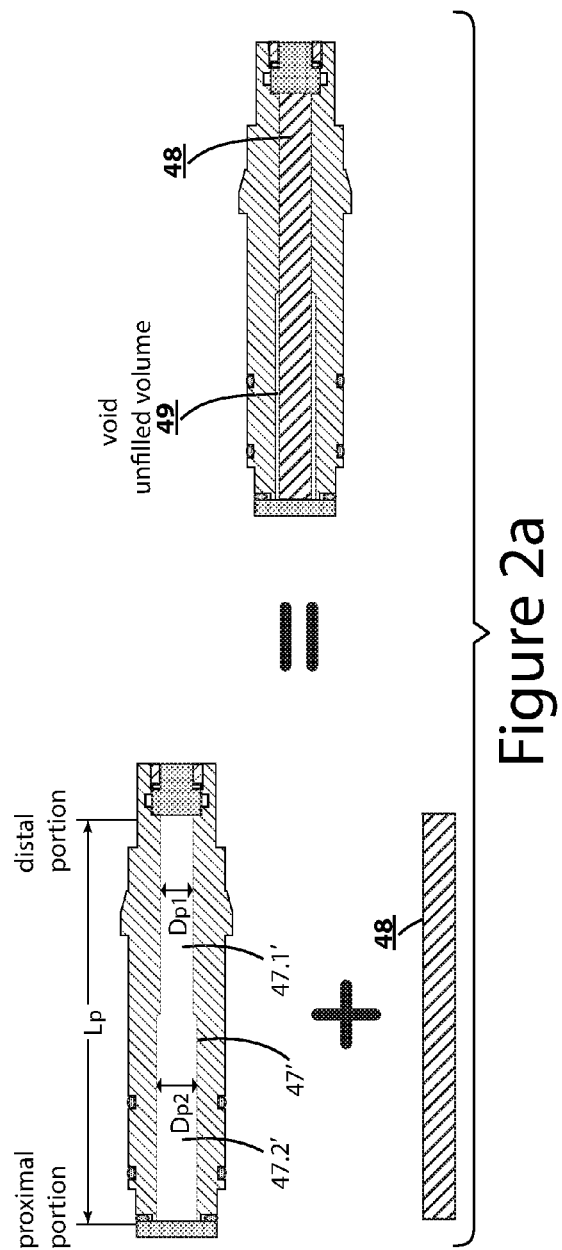

OPTICAL TRANSMISSION CELL WITH MINIMIZED SPURIOUS ABSORPTION

CROSS REFERENCE TO RELATED APPLICATIONS

This application claims the benefit of U.S. Provisional Patent Application Ser. No. 61/954,464, filed Mar. 17, 2014.

BACKGROUND OF THE INVENTION

Field of the Invention

The invention relates generally to seals for spectroscopic measuring devices and, more particularly, to an optical transmission cell with minimized spurious absorption.

Description of the Related Art

Spectroscopic measuring devices are often used to analyze gasses. The purpose of this invention is to solve a problem that has arisen in the production of transmission cells for the analysis of gasses using near infrared spectroscopy. The problem will be discussed with reference to FIG. 1 which shows a transmission cell 110, transmission cell system 110, that is designed for analyzing a gas via operative connection to a spectrometer (not shown). As shown, the preferred transmission cell 110 consists of three major subassemblies: a central section or body 20 formed from a standard Swagelok® cross fitting, and first and second optical probes 40, 50 which are directed toward each other across the central "cross" of the cross fitting 20.

The transmission cell 110 functions as follows: Near-IR radiation (which we will refer to as "NIR light" or just "light") enters the system 110 by means of a transmitting fiber-optic cable (not shown, but alluded to with the inbound arrow labeled "NIR Light" on the left of FIG. 1). This fiber is terminated into the first optical probe 40 at a fiber-optic connector 41. The light diverging from the end of the transmitting fiber is collected by a lens 42 so as to form a nominally collimated beam that is directed through an interior of the first probe 40 (region 1), through a measurement space in the cross fitting or cell body 20 (region 2), and then through an interior of the second probe 50 (region 3) where it collected by a second lens 52 and focused on a receiving optical fiber (not shown, but alluded to with the outbound arrow labeled "NIR Light" on the right side of FIG. 1). The receiving fiber would be located in connector 51 in the same manner that the transmitting fiber would be located in connector 41.

A total of four optical windows 44, 45, 54, 55 are included in the preferred transmission cell 110. The number is four because each probe 40, 50 has two windows—a primary one and a secondary one. In more detail, the first probe 40 has a primary window 44, and a secondary window 45 and the second probe 50 has a primary window 54 and a secondary window 55.

As further shown in FIG. 1, the two primary windows, 44 and 54 face one another from opposite sides of the nominal measurement region (region 2). The primary windows 44, 54 are preferably sealed into the tips of the first and second probe bodies 40, 50 using Axiom's patented welded sealing technique utilizing metal "C" rings 43 and 53 coated with a compliant material such as PTFE or Gold. These seals are designed to withstand the high pressures that may be present in the measurement region (region 2) and are explained in more detail in U.S. Pat. No. 6,587,192 hereby incorporated by reference as if fully set forth herein.

The secondary windows 45 and 55 are located near the outer ends of the first and second probes 40, 50. The purpose of these secondary windows 45, 55 is to isolate the probe interiors (regions 1 and 3) from contaminants that may be present in the ambient air. The space between the primary and secondary windows, i.e. between windows 44 and 45 and between windows 54 and 55, forms the interior of a given probe (regions 1 and 3). Each region has a diameter and a length which we will specify as Dp and Lp, respectively.

As further shown in FIG. 1, the probes 40, 50 are characterized by interiors, bores, or unfilled volumes 47, 57 in regions 1 and 3. It would be desirable to minimize Lp as much as possible to minimize the effects of any undesired gasses in the probe body 40 or 50. However, a practical minimum value is placed on Lp by the fact that the probes 40, 50 must interconnect, e.g. have some length to mate to the mechanical dimensions of the Swagelok cross 20 with threaded fasteners (not separately numbered). The effects of undesired gasses within the interiors, bores, or unfilled volumes 47, 57 of the probes 40, 50 could also be minimized by continuously pumping on the probes 40, 50 or purging them. However, this is not practical in many situations such as when the systems 110 are located in the field, such as at natural gas wells. At first blush, the only practical approach in such case is to first evacuate the interior of the probes 40, 50 and then back fill them with an inert gas such as nitrogen.

Even though the seals 43, 53 have extremely low leak rates, the vapor in the cell body 20 is often at very high pressure relative to the pressures in the probe bodies 40, 50, such that over time small amounts of gas will inherently leak into the probe bodies 40, 50. This will create measurement problems because the measurements are very sensitive to small changes in the NIR spectrum.

There remains a need, therefore, for a spectroscopic measuring devices such as a transmission cell that resolves such problems, i.e. that minimizes spurious absorption due to such leakage.

BRIEF SUMMARY OF THE INVENTION

In accordance with the present invention, structure are disclosed which overcome these problems.

In a first aspect, the invention resides in a spectroscopic measuring device for minimizing the effect of undesired gases that that interferes with measurement, comprising: a probe body that is inherently subject to leakage of undesired gas, the probe body having an axis, a distal end, a proximal end, and an interior; a primary window disposed at or near the distal end of the probe body and sealed with respect to the probe body; a secondary window located at or near the proximal end of the probe body and sealed with respect to the probe body, a bore defined by the interior of the probe body between the primary window and the secondary window, the bore having a nominal length and a nominal volume; a filler rod located in the bore and capable of transmitting light entering the primary window along the nominal length of the bore; and a void located adjacent to the filler rod, the void increasing the nominal volume of the bore.

In a second aspect, the invention resides in a spectroscopic measuring device for minimizing the effect of undesired gases that that interferes with measurement, comprising: a central section for receiving a gas to be analyzed; and first and second probe bodies that are inherently subject to leakage of undesired gas, wherein the first and second probe bodies are attached to the central section with one injecting light into the central portion and one collecting light from the central portion in order to measure a characteristic of a gas passing through the central section, and wherein each probe body comprises an axis, a distal end, a proximal end, and an interior; a primary window disposed at or near the distal end of the probe body and sealed with respect to the probe body; a secondary window located at or near the proximal end of the probe body and sealed with respect to the probe body, a bore defined by the interior of the probe body between the primary window and the secondary window, the bore having a nominal length and a nominal volume; a filler rod located in the bore and capable of transmitting light entering the primary window along the nominal length of the bore; and a void located adjacent to the filler rod, the void increasing the nominal volume of the bore.

The invention, now having been briefly summarized, may be better visualized by turning to the following drawings wherein like elements are referenced by like numerals.

DESCRIPTION OF THE DRAWINGS

The preferred embodiments of the just summarized invention can be best understood in connection with a detailed description of the following figures.

FIG. 1 is a schematic cross-sectional view of a transmission cell 110 of a first construction having a centrally located cell body 20, first probe 40 with a bore 47, and second probe 50 with a bore 57, and where the bores 47, 57 of the first and second probes 40, 50 (Regions 1 and 3) are unfilled and subject to spurious absorption due to the presence of undesired gasses therein;

FIG. 1a is a simplified portion of the first probe 40 from FIG. 1 showing that its bore 47 has a length Lp and a diameter Dp, a glass rod 48 that fits tightly within the bore 47, and the resulting assembly which has virtually no unfilled volume;

FIG. 2 is a schematic cross-sectional view of a transmission cell 210 of a second modified construction where the reference numbers to items similar to corresponding items in FIG. 1 have been omitted for clarity, and where the bores 47', 57' of the first and second probes 40, 50 (Regions 1 and 3) have been modified to contain filler rods 48, 49, and to have unfilled voids 49, 59 of increased volume; and FIG. 2a is a simplified portion of the first probe 40 from FIG. 2 showing that its bore 47' has a length Lp and two diameters, a first diameter Dp1 at a distal portion of the bore 47' and an increased diameter Dp2 along a portion of its length at a proximal portion of the bore 47', a glass rod 48 that fits within the bore 47', and the resulting assembly which includes a void or unfilled volume 49.

DETAILED DESCRIPTION OF THE PREFERRED EMBODIMENTS

To better understand the preferred embodiments of the invention that resolve the spurious absorption problem that we have encountered, we need to introduce the concept of Beer's Law. This states that the optical absorption by a material can be specified in terms of an Absorbance (A) which is proportional to concentration of the material (C) and the pathlength (L). i.e.

$$A_c = a_c L_c C_c, \text{ where the subscript "c" refers to the cell.} \quad \text{Eq. 1}$$

Here, $a_c$ is an absorption coefficient for the material in the cell.

A similar expression, except with subscript "c" replaced by subscript "p" would apply to material in the probe body.

The transmission through a volume is related to the Absorbance by the following expression:

$$T = -\log_{10} A. \quad \text{Eq. 2}$$

In many applications, such as natural gas analysis, the vapor in the cell body will be at a high pressure. The pressure is related to concentration by the ideal gas law:

$$P = CRT, \quad \text{Eq. 3}$$

where, R=the gas constant, and T=temperature.

Here, the concentration is given by C=n/V, where, n=number of moles of the gas and V=volume. For a given pressure differential, DP, between the cell and the probe body, the rate of flow from the cell to the probe, F, can be stated as:

$$F = K_D P, \quad \text{Eq. 4}$$

where "K" is a constant that takes into consideration the cross sectional area and the leakage characteristics of the window seal.

As long as temperature is constant and the pressure in the probe body is very low compared to that in the cell, DP will be constant and the gas pressure in the probe will build up linearly over time:

$$P_p(t) = (K_D P/V_p)t, \quad \text{Eq. 5}$$

Where Vp is the volume of the probe body.

The concentration will be:

$$C_p(t) = P_p(t)/RT = (K'_D P/V_p)t, \text{ where } K' = K/RT \quad \text{Eq. 6}$$

The optical absorbance will be given by the expression $$A_p(t) = a_p L_p C_p(t) = a_p L_p (K'_D P/V_p)t = a_p K'_D P(L_p/V_p)t. \quad \text{Eq. 7}$$

In other words, the absorbance is proportional to the pathlength and inversely proportional to the volume as long as the pressure in the probe remains low compared to that in the measurement cell.

Even though the leak rates through the coated metal seals are usually very low, the buildup of small amounts of gas in the probe bodies over time can lead to measurement problems. This is due to the sensitivity of the measurements to small changes in the near-infrared spectrum.

With the foregoing observations in hand, one can see how the embodiment of FIG. 2 offers a significant solution to the problem of spurious absorption. In particular, the second transmission cell system 210 of FIG. 2 substantially reduces the effects of gas leakage into the probe bodies 40, 50 by minimizing the ratio of pathlength to probe volume, i.e. ($L_p/V_p$). The first step is to place a glass rod 48, 58 in the probe body 40, 50) so that most of the optical path is within the rod 48, 58 rather than in to open volume of the probe 40, 50. The simplest way to do this is to slip a tight-fitting rod 48, 58 into the bore 47, 57 of the previously existing probes. However, the use of a filler rod 48, 58 does not by itself solve the problem since it reduces the volume of the bore 47, 57 almost as much as the pathlength. i.e. for a tight fitting rod, the unfilled volume will be $$V_u = (pD_p^2/4)L_u, \quad \text{Eq. 8}$$

Where $L_u$ is the length of the unfilled volume 49 and, again, $D_p$ is the inner diameter of the probe. The ratio of pathlength to cell volume is $$Lu/Vu = 4/\pi D_p^2$$

Thus, substituting Eq. 9 into Eq. 7, we see that the Absorbance is independent of pathlength.

Our solution to this problem is to increase the volume of the probe that lies outside of the glass rod. This can be done within the mechanical constraints of the probe design by increasing the bore diameter for a portion of its length.

The design illustrated in FIG. 2 increases the probe volume by about two orders of magnitude compared to the volume between the ends of the rod and the probe windows. It should thus reduce the absorbance by two orders of magnitude. The glass rod is indicated by 48 or 58. The increased volume provided by discrete or annular voids located adjacent to the filler rod 48 or 58 is indicated by 49 or 59.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. The claims are thus to be understood to include the specifically illustrated and described embodiments, structures based on equivalents concepts, and substitutions that incorporates the invention. For example, the probe volume can also be increased by creating an additional volume away from the main body of the probe. This can be done, for example, by providing a significant length of tubing between the probe bore 47, 57 and the valve used for sealing the probe.

The invention claimed is:

1. A spectroscopic measuring device for minimizing the effect of undesired gases that that interferes with measurement, comprising:
   a central section for receiving a gas passing through the central section to be analyzed;
   first and second probe bodies that are inherently subject to leakage of undesired gas, wherein the first and second probe bodies are attached to the central section with one injecting light into the central section and one collecting light from the central section in order to measure a characteristic of the gas passing through the central section, and wherein each probe body comprises:
   an axis, a distal end, a proximal end, and an interior;
   a primary optical window disposed at or near the distal end of the probe body and sealed with respect to the probe body;
   a secondary optical window located at or near the proximal end of the probe body and sealed with respect to the probe body, a bore in the interior of the probe body that defines an optical path between the primary optical window and the secondary optical window, the bore having a nominal length and a nominal volume;
   a filler rod located in the bore and capable of transmitting light entering the primary optical window along the nominal length of the bore; and
   a void in fluid communication with the bore and located adjacent to the filler rod and outside of the optical path, the void increasing the nominal volume of the bore and providing a location for holding undesired gas outside of the optical path;
   wherein each filler rod fits tightly within a first portion of the bore and wherein each void comprises an expanded space in a second portion of the bore.

2. The spectroscopic measuring device of claim 1, wherein the primary optical window of each probe body is sealed with respect to the respective probe body by a high pressure seal comprising a "C"-ring.

3. The spectroscopic measuring device of claim 1 wherein each filler rod is a glass rod.

4. The spectroscopic measuring device of claim 1 wherein each void comprises an expanded space around a portion of the filler rod.

5. The spectroscopic measuring device of claim 1 wherein the first portion is a distal portion of the bore and wherein in the second portion is a proximal portion of the bore.

6. The spectroscopic measuring device of claim 5 wherein each bore has a first diameter in the distal portion and a second larger diameter in the proximal portion, the void being formed by the second larger diameter in the proximal portion.

7. The spectroscopic measuring device of claim 1 wherein the central section comprises a cross fitting.

8. The spectroscopic measuring device of claim 1 wherein the light comprises near-infrared radiation.

* * * * *